United States Patent [19]
Taboada et al.

[11] Patent Number: 5,318,022
[45] Date of Patent: Jun. 7, 1994

[54] METHOD AND APPARATUS FOR DETERMINING HEMOGLOBIN OXYGENATION SUCH AS IN OCULAR AND OTHER VASCULAR BEDS

[76] Inventors: John Taboada, 12530 Elm Country La., San Antonio, Tex. 78230; Daniel R. Peters, 6111 Sundial, San Antonio, Tex. 78238

[21] Appl. No.: 663,115

[22] Filed: Mar. 1, 1991

[51] Int. Cl.$^5$ .............................. A61B 5/00; A61B 6/00
[52] U.S. Cl. .................................... 128/633; 128/634; 128/664; 128/665
[58] Field of Search ........................... 128/633-634, 128/664-665; 356/40"41, 39, 42

[56] References Cited

U.S. PATENT DOCUMENTS

| | | | |
|---|---|---|---|
| 4,223,680 | 9/1980 | Jöbsis | 128/633 |
| 4,569,354 | 2/1986 | Shapiro et al. | 128/665 |
| 5,072,731 | 12/1991 | Taratuta et al. | 128/665 |
| 5,119,814 | 6/1992 | Minnich | 128/633 |

*Primary Examiner*—David Isabella
*Assistant Examiner*—P. Zuttarelli
*Attorney, Agent, or Firm*—Baker & Botts

[57] ABSTRACT

An oximetry technique permits determination of hemoglobin oxygenation in vascular beds such as the inner retinal capillary beds. For a retinal application, an oximeter (FIG. 2) uses as a probe light source a multiline argon laser (11) that operates at three wavelengths in the hemoglobin absorption band, preferably 488, 501, and 514 nm. The oximeter optics module (30) attaches to the output end of a conventional slit lamp microscope (20). Reflected probe light is separated (34) into its constituent wavelengths, and photon counters (38) are used to measure light intensity for each wavelength. Data acquisition and analysis are performed by an oximeter processor (40) that computes hemoglobin oxygenation ratios from the intensity measurements, and determines the corresponding percent oxygen saturation.

22 Claims, 2 Drawing Sheets

METHOD AND APPARATUS FOR DETERMINING HEMOGLOBIN OXYGENATION SUCH AS IN OCULAR AND OTHER VASCULAR BEDS

TECHNICAL FIELD OF THE INVENTION

The invention relates generally to optical hemoglobin oximetry by which light is used to measure hemoglobin oxygenation, and more particularly relates to a method and apparatus for performing hemoglobin oximetry in optically accessible tissues such as ocular and other vascular beds. In an exemplary application, optical oximetry is performed using a multi-line (three wavelength) laser probe operating in the absorption band (around 500 nm) to determine the level of oxygen saturation in the capillary beds of the inner retina.

BACKGROUND OF THE INVENTION

The retina is supplied with oxygen through both choroidal and retinal circulation. Oxygen diffusion from the choroid supplies oxygen to the avascular outer retina and photoreceptors, while the inner retina and nerve fiber layer is supplied with oxygen via the retinal vascular system (arteries, veins and capillary beds).

Like other neural tissues, the retina is very metabolically active and has a high oxygen demand. Consequently, diseases that alter retinal circulation, such as diabetic retinopathy, sickle cell disease, hypertension, and vascular occlusive diseases, result in impaired oxygen delivery. As a consequence, optical function can be significantly impaired, and severe damage to retinal tissues can occur.

The specific problem to which the invention is applicable is optical retinal oximetry—the use of noninvasive optical means to determine hemoglobin oxygen saturation in the inner retina. More generally, the invention is applicable to optical hemoglobin oximetry techniques f or use with any tissues (such as vascular beds) that are optically accessible.

In the context of the specific problem, retinal oximetry techniques have been used in the clinical evaluation of retinal diseases such as diabetic retinopathy. In diabetes, progressive retinal vascular disease leads to retinal ischemia, which in turn induces production of vasoproliferative factor that eventually results in neovascularization with its multiple complications. (References 1,2,3,4 at the end of the Background). The current front line treatment for neovascularization is laser panretinal photocoagulation (PRP). This treatment modality has proven to be extremely effective, but exactly why it is effective is unclear. (References 5,6,7,8)

Three proposed mechanisms may contribute to the regression of diabetic retinal neovascularization to greater or lesser degrees. The first of these suggests that the total retinal metabolic demand is reduced by ablating hypoxic retinal tissue with PRP. The second proposes that the PRP scars somehow alter the circuitory relationship between the choroid and hypoxic inner retina thereby allowing improved oxygen delivery. Alternatively, it has been found that laser scars cause the retinal pigment epithelium (RPE) to release a protein that directly inhibits neovascularization.

It seems likely that more than one, if not all, of these mechanisms contribute to neovascular regression post PRP treatment. What has been lacking is an accurate and available means by which to evaluate retinal metabolism, oxygenation and development of neovascularization.

Invasive techniques to provide such information are not practical for routine clinical use or research. Consequently, several techniques for noninvasive evaluation of retinal metabolism have been developed.

The first of these has looked at retinal blood flow as a measure of retinal metabolism. (References 9,10) Efforts to noninvasively evaluate retinal oxygen metabolism remained relatively stagnant however, until the principles of optical hemoglobin oximetry were first applied to the retina in 1963. (Reference 11)

Techniques for optical oximetry have been evolving, and have been applied to both animals and humans. (References 12,13) Early efforts were based on using only two wavelengths of light filtered from incandescent light sources. Unfortunately, this led to inaccurate results because of the Lambert-Beer Law, which strictly limits two wavelength oximetry to only hemolyzed solutions.

In 1975, these limitations for non-hemolyzed blood were overcome by the development of an accurate three-wavelength technique for the measurement of percent oxyhemoglobin. (Reference 14) Three-wavelength oximetry is based on several important principles. The first of these states that light absorption by blood depends on $O_2$ Sat and wavelength. Second, a relationship exists between a measurable optical quantity like optical densities and the extinction coefficient of the mixture of oxyhemoglobin ($HbO_2$) and deoxyhemoglobin (Hb) at a given $O_2$ Sat. (Reference 15) Finally, optical densities at two specific wavelengths can be compared to the optical density at a third specific wavelength and hemoglobin absorption values may then be calculated and used to accurately obtain percent $O_2$ Sat. (Reference 14)

The relationship between the extinction coefficients of $HbO_2$ and Hb in the visible spectrum are available for use when calculating percent $O_2$ Sat. The advantages and disadvantages of these wavelengths using existing technology have previously been explored. (References 16,17)

In particular, wavelength selection criteria for retinal oximetry have been based on inherent characteristics of retinal tissue and blood. Wavelengths significantly below 520 nm have not been explored because of strong absorption by hemoglobin, leading to relatively low retinal tissue reflectance, which would require intense polychromatic illumination.

Three wavelength oximetry has been adapted to real-time measurements of retinal vessel oxygen saturations ($O_2$ Sat). (References 15,16,17) These retinal oximeters use a bright source of non-collimated light (typically a broad spectrum halogen or arc light) that is filtered to provide three selected wavelengths—the light source and the filters are cooperatively selected to provide at least one isobestic wavelength (i.e., a wavelength at which hemoglobin absorption is essentially independent of 02 Sat) and at least one wavelength for which blood absorption is dependent upon $O_2$ Sat.

To probe a selected area of the retina, the light is focused on either a large caliber retinal artery or a large caliber retinal vein. The percent $O_2$ Sat is calculated from measurements of the light reflected from either the artery (in which hemoglobin oxygenation is relatively high) or the vein (in which hemoglobin oxygenation is relatively low), and from the RPE background.

This technique for performing retinal oximetry is disadvantageous in several respects. It is complicated to control, requiring precise focusing on retinal blood vessels and a complicated filtering to produce a multiwavelength probe. It limits percent $O_2$ Sat measurements to large caliber blood vessels, and does not allow $O_2$ Sat measurements to be made in the intraretinal capillary beds. It is based on measuring reflected light, and therefore uses wavelengths up in the reflectance (or partial transmittance) band above 600 nm, which tend to yield low contrast for the vascular blood column, and to provide less uniform reflections with variable background fundus pigmentation. Because, it requires a bright light source (to ensure adequate reflectance for measurement), it has a tendency to probe the sub-retinal choroidal blood, which makes it difficult to isolate the retina for $O_2$ Sat measurement.

Optical oximetry techniques have been used to determine hemoglobin oxygenation in non-ocular tissues. For example, optical oximeters are used to measure oxygen saturation in relatively thin tissues (such as the ear lobe or the finger) through which probe light of wavelengths substantially longer than 520 nm can be transmitted. Because of the high level of optical absorption in hemoglobin even for wavelengths longer than 520 nm, the reliance on the transmission of probe light through the tissue significantly restricts the applications for these oximetry techniques.

Accordingly, a need exists f or an improved optical oximetry technique, one that has specific applicability to determining hemoglobin oxygenation in the capillary beds of the inner retina, and more general applicability to other light-accessible tissues.

References

1. Michaelson IC: Retinal circulation in man and animals. Springfield, Ill.: Thomas, 1954, 118–131
2. Aston N: Studies of the retinal capillaries in relation to diabetic and other retinopathias. Br. J. Ophthalmol 47:521, 1963
3. Ashton N: Retinal vascularization in health and disease. Am J Ophthalmol 44:7, 1957
4. Kohner EM, Shilling JS, Hamilton AM: The role of avascular retina in new vessel formation. Metabolic Ophthalmol 1:15, 1976
5. Beetham WP, Aiello LM, Balodimos MC, Konecz L: Ruby laser photocoagulation of early diabetic neovascular retinopathy. Arch Ophthalmol 83:261, 1970
6. Wetzig PC, Jepson CN: Treatment of diabetic retinopathy by light coagulation. Am J Ophthalmol 65:459, 1966
7. The Diabetic Retinopathy Study Group: Photocoagulation treatment of proliferative diabetic retinopathy: The second report of Diabetic Retinopathy Study findings. ophthalmology 85:82, 1978
8. Glaser BM, Campochiaro PA, Davis JL Jr., Satom M: Retinal pigment epithelial cells release and inhibitor of neovascularization. Arch Ophthalmol 103:1870–1875, 1985
9. Hickham JB, Frayser R: A photographic method for measuring the mean retinal circulation time using fluorescein. Invest Ophthalmol 4:876, 1965
10. Feke CT, Goger DG, Tagawa H, Delori FC: Laser doppler technique for absolute measurement of blood speed in retinal vessels. IEEE Trans Biomed Eng BE-34: 673, 1987
11. Hickham JB, Frayser R, Ross JC: A study of retinal venous blood oxygen saturation in human subjects by photographic means. Circulation 27, 375, 1963
12. Hickham JB, Frayser R: Studies of the retinal circulation in man: observation of vessel diameter, arteriovenous oxygen saturation difference, and mean circulation time. Circulation 33, 302, 1966
13. Laing RA, Cohen AJ, Friedman E: Photographic measurements of retinal blood oxygen saturation: Falling saturation rabbit experiments. Invest Ophthalmol 14:606, 1975
14. Pittman RN, Duling BR: A new method for the measurement of percent oxyhemoglobin. i Appl Physiol 38:315, 1975
15. Van Assendelft OW: Spectrophotometry of hemoglobin derivatives. Springfield, IL: Thomas 1970, pp 321–352
16. van Norren D, Tiemeijer LF: Spectral reflectance of the human eye. Vision Res 26:313, 1986
17. Delori FC, Pflibsen K: Spectral reflectance of the human ocular fundus. (in preparation)
18. Delori FC: Noninvasive technique for oximetry of blood in retinal vessels. Appl Opt 27:1113, 1988
19. Delori FC, Rogers FJ, Bursell SE, Parker JS: A system for non-invasive oximetry of retinal vessels. In Frontiers of Engineering in Health Care, 1982. Proceedings, Fourth Annual Conference of the I.E.E.E. Engineering in medicine and Biology Society. Potvin AR, Potvin JH (eds): Institute of Electrical & Electronics Engineers, New York, p. 296, 1982
20. Delori FC, Weiter JJ, Mainster MA, Flook VA: Oxygen saturation measurements in retinal vessels. Invest Ophthalmol. Visual Sci (ARVO Suppl) 13, 1983

SUMMARY OF THE INVENTION

The invention is an optical oximeter for determining hemoglobin oxygenation in tissues that are optically accessible (including sub-cutaneous tissues accessible by endoscope). In an exemplary application, a laser oximeter operating in the absorption band is used to probe the capillary beds of the inner retina. The term laser is used to designate a collimated light source in general, unless a more specific meaning is indicated.

The oximetry technique of the invention comprises: (a) probing a selected area of tissue with a probe light of at least two wavelengths, at least one of which is isobestic and at least one of which is non-isobestic; (b) detecting the intensity of reflection for each wavelength of the probe light; and (c) determining from the reflected intensities appropriate ratios representative of oxygen saturation.

In one aspect of the invention, the probe light is collimated. In another aspect of the invention, the probe light wavelengths are in the hemoglobin absorption band. In still another aspect of the invention, the oximetry technique is used to determine hemoglobin oxygenation in vascular beds (such as the capillary beds in the inner retina).

In more specific aspects of the invention, for an exemplary application of the oximetry technique to hemoglobin oxygenation in the capillary beds of the inner retina, a laser oximeter uses as a probe light source a three-wavelength argon laser that operates in the hemoglobin absorption band, with one isobestic wavelength at about 501 nm and two non-isobestic wavelengths at about 488 nm and 514 nm.

The laser oximeter includes an oximetry optics module that is designed to be installed as a simple retrofit for a conventional slit-lamp microscope. Laser probe light directed to a selected area of the retina is partially reflected from the capillary beds back through the microscope to the oximetry optics.

The oximetry optics includes both separation optics and an intensity detector. The separation optics separates the reflected light into the three different wavelengths. The intensity detector includes a separate intensity detection channel for each wavelength, and uses photon counters in each channel to provide a corresponding reflection signal.

The oximeter processor computes two oxygen saturation ratios: a ratio R1 equal to the ratio of the reflection intensity for one non-isobestic wavelength to the reflection intensity for the isobestic wavelength, and a ratio R2 equal to the ratio of the reflection intensity for the other non-isobestic wavelength to the reflection intensity for the isobestic wavelength. The oximeter processor is coupled bidirectionally to the oximeter optics —it controls the oximeter optics, receives the output from the photon counters, and computes the oxygen saturation ratios. In addition, the oximeter processor can be programmed to implement an oximeter scanning program in which the probe light is scanned in a predetermined pattern around the eye to produce an oximetric map.

The technical advantages of the invention include the following. The probe site can be illuminated by a bright but physiologically safe collimated light source that produces plentiful reflectance for sensitive oximetry measurements and calculations. Operation in the hemoglobin absorption band (wavelengths near 500 nm) necessarily reduces retinal penetration, thereby providing inner retinal (as opposed to retinal and choroidal) hemoglobin oximetry measurements. Probing vascular beds eliminates the need to precisely focus on large caliber arteries and veins. Moreover, for the retinal oximetry application, probing the capillary beds enables evaluation of the macular region of the retina.

The oximeter can use a conventional laser source as a probe light, and in particular the selection of an argon laser as a probe light source results in the wavelength composition (488 nm, 514 nm, and the isobestic wavelength 501 nm) in the hemoglobin absorption band that is ideally suited for oximetry measurements. The oximetry optics module can be readily installed as an optical retrofit to a conventional slit-lamp microscope.

A more complete description of the invention, as well as further features and advantages, are provided by the Detailed Description of exemplary embodiments of the invention, read in conjunction with the accompanying Drawings. Although the Detailed Description and the Drawings are directed to specific exemplary embodiments, various modifications of these exemplary embodiments, as well as alternative embodiments, will be suggested to those skilled in the art, and it is to be understood that the invention encompasses any modifications or alternative embodiments that fall within the scope of the appended Claims.

DETAILED DESCRIPTION OF THE INVENTION

The Detailed Description of an exemplary embodiment of the oximeter is organized as follows:
1. Oximetry Technique
2. Laser Oximeter
2.1. Laser Probe
2.2. Oximeter Optics
2.3. Oximeter Processor
3. Alternative Embodiments The exemplary laser oximeter uses a multi-line argon laser probe operating in the hemoglobin absorption band to provide measurements of hemoglobin saturation in the capillary beds of the inner retina, such as for PRP therapy for diabetic retinopathy both pre- and post-treatment. However, the invention has general applicability for probing optically accessible tissues (such as vascular beds).

1. Oximetry Technique. The exemplary laser oximetry technique comprises: (a) probing a selected capillary bed with a multi-line argon laser that provides three wavelengths in the hemoglobin absorption band, one of which is isobestic; (b) detecting the intensity of reflection for each wavelength of the probe light using separate photon counters; and (c) determining from the photon counter output appropriate oxygen saturation ratios representative of oxygen saturation in the capillary bed.

Figure 1:
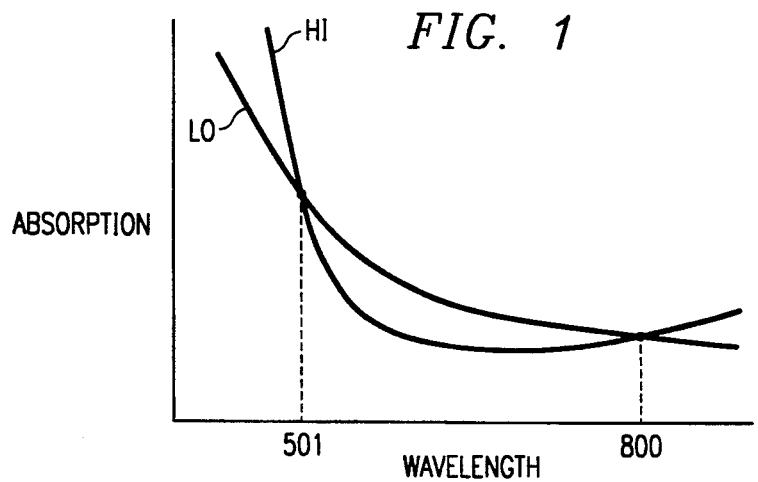
FIG. 1 is an illustrative plot of Hi-oxygenation and Lo-oxygenation curves of blood absorption versus probe light frequency for the exemplary capillary bed application of the laser oximeter.

FIG. 1 provides an absorption versus probe wavelength plot that illustrates the selection of the wavelengths for the argon laser probe in the context of the exemplary retinal capillary bed application. The plot contains two curves: a High-oxygenation curve HI, and a Low-oxygenation curve Lo.

The HI and LO curves intersect at probe wavelengths of approximately 501 nm and approximately 800 nm which are designated isobestic wavelengths, i.e., wavelengths at which absorption of the probe light essentially independent of hemoglobin oxygenation. The wavelengths around the 501 nm isobestic wavelength are designated the absorption (or soret) band because of the relatively higher level of absorption for both High- and Low-oxygenated hemoglobin, while the wavelengths around the 800 nm isobestic wavelength are designated the partial transmittance band because of the relatively low level of absorption.

As described in the background, wavelength selection criteria for retinal oximetry is based on the inherent characteristics of retinal tissue and blood. The exemplary oximetry technique uses probe light wavelengths that are in the absorption band below about 520 nm, which includes the 501 nm isobestic wavelength. Operation in the absorption band significantly reduces penetration of the probe light to tissue layers below the capillary bed under evaluation, and thereby significantly reduces unwanted reflections from those tissue layers. Indeed, for the exemplary retinal oximetry application, these wavelengths are severely absorbed in the RPE layer below the inner retina, essentially isolating the capillary beds under evaluation.

Coincidentally, a multi-line argon laser outputs a wavelength of 501 nm, as well as wavelengths of 488 nm and 514 nm, both of which are within the absorption band. Thus, the selection of an argon laser for the probe source satisfies the two parameters of probe wavelength selection for the exemplary retinal capillary bed application: operation in the absorption band with at least one isobestic wavelength.

Figure 2:
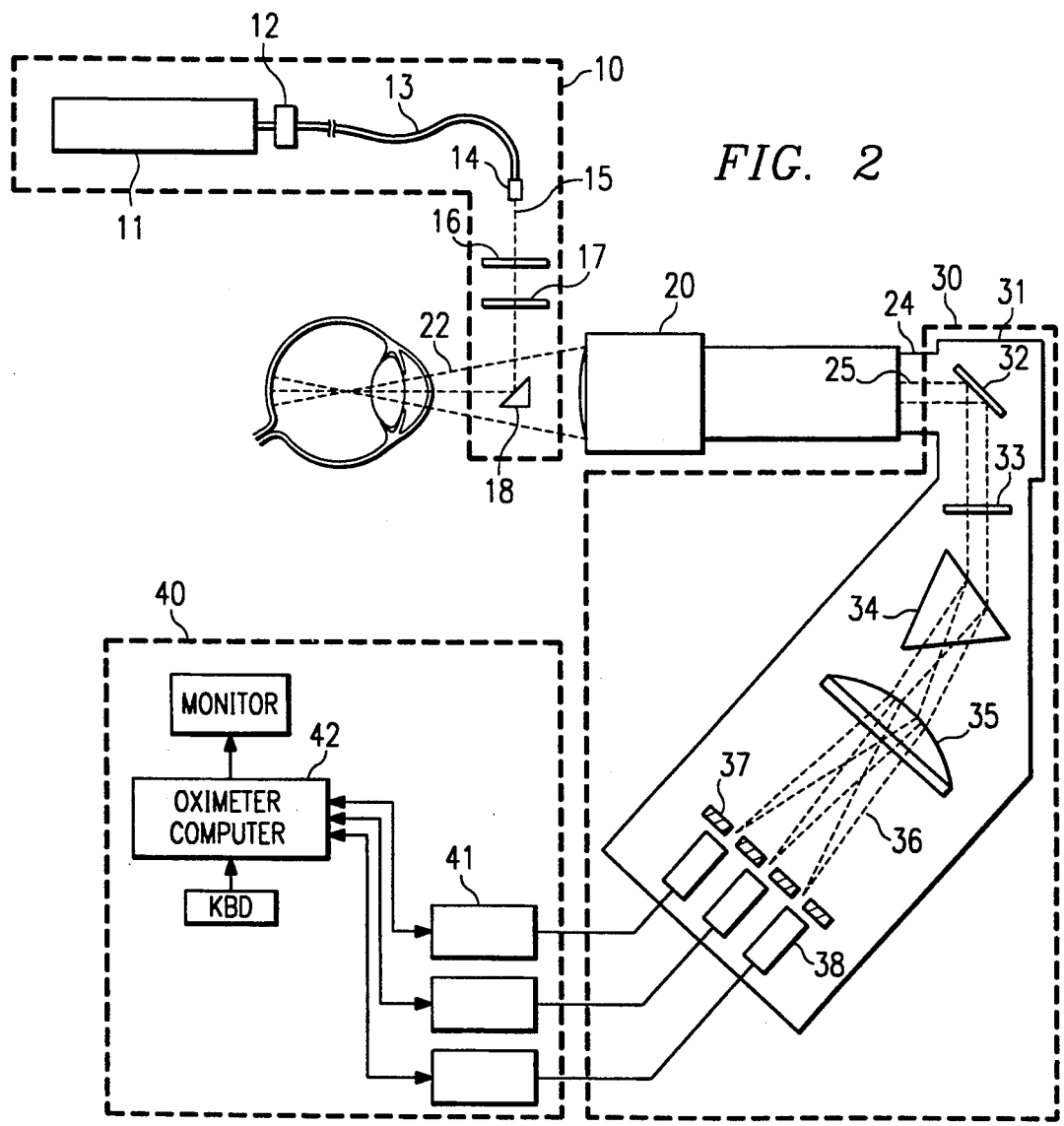
FIG. 2 is a schematic diagram of the exemplary laser oximeter using a three-wavelength argon laser as a probe light source, with the oximeter optics being optically coupled to the eyepiece end of a conventional slit lamp microscope ocular tube.

2. Laser Oximeter. FIG. 2 provides a schematic of the exemplary laser oximeter, including a laser probe 10, a microscope 20, an oximeter optics module 30, and an oximeter processor 40.

2.1. Laser Probe. Laser probe 10 includes an argon-ion laser 11 to provide a source of collimated probe light. This type of laser is used conventionally for retinal photocoagulation, and has multiple characteristic emission wavelengths, including 488 nm, 501 nm, and 514 nm.

The probe light output of the argon laser 11 is coupled through an input port lens 12 into an optical fiber 13. The optical fiber carries the probe light to the output port lens 14, and the probe light emerges along 15. As with conventional photocoagulation instruments, the laser radiation is attenuated by a filter 16, which reduces the beam intensity to the level of typical radiation-treatment aiming applications.

The low intensity beam is passed through a polarizer 17, and directed by a reflector 18 into the patient's eye. The optics of the eye focuses the light to a small spot 15 in a selected area of the retina.

The laser probe light can be controlled to probe areas accessible to the aiming beam of conventional argon-ion laser photocoagulators. It requires no additional light other than that provided by the laser aiming illuminator.

Alternatively, probe light can be provided by any other source of collimated light that provides multiple wavelengths in the selected band.

2.2. Oximeter Optics. The exemplary oximeter optics module 30 is designed to be installed as a retrofit into the existing ocular tube of a conventional argon-ion laser slit lamp microscope, indicated at 20. The eyepiece (ocular) of the microscope is removed, and the oximeter optics module is fitted to the output distal end.

The laser probe light is scattered from the retina (i.e., the selected capillary bed area), so that reflected probe light 22 exits the eye. This reflected probe light is collected by the microscope 20, and focused. At the output distal end 24 of the microscope, the reflected probe light 25, is input to the oximeter optics module 30.

The oximeter optics module 30 is housed in a light tight enclosure 31. The reflected probe light entering the oximeter optics module is reflected from mirror 32, through a polarization analyzer 33. The polarization analyzer is arranged such that the reflected probe light it passes is polarized at right angles to the laser probe light 15 directed into the eye. This polarized arrangement helps reject unwanted partial reflections from the corneal surface and from the inner limiting membrane.

The analyzed reflected probe light is then passed into a dispersing prism 34, which separates the three characteristic reflected wavelengths (i.e., 488 nm, 501 nm, and 514 nm) into three corresponding reflected probe light paths 36. Each of the separate reflected probe light beams is then passed through a 3-aperture plate 37, which reduces stray light and channels the beams into respective intensity detectors 38. Alternatively, a grating can be used for the dispersing component.

The exemplary oximeter optics uses photon counting to provide an accurate measure of reflected intensity. Conventional photon counters such as photomultipliers may be used. Alternatively, photodiodes such as RCA SPCM-100 may be used.

Each photon counter 38 outputs a continuous photon count signal for a respective reflected probe light beam, i.e., for a respective wavelength.

2.3. Oximeter Processor. The oximeter processor 40 includes electronic counters 41 and a computer 42.

The photon count signal from each of the photon counters 38 is input to a respective conventional digital counter 41. These counters provide an accurate digital count for respective photon count signals.

Computer 42 is bidirectionally coupled to each of the digital counters 41, enabling it to both reset and read each counter. In particular, the computer is able to read the digital counts that are a measure of the respective intensities of the reflected probe light beams, as detected by the photon counters 38.

The oximeter processor (computer 42) is programmed to calculate the oxygen saturation ratios:

$$R_1 = \frac{N_{488}}{N_{501}}$$

$$R_2 = \frac{N_{514}}{N_{501}}$$

where $N_0$ are the digital counts corresponding to the photon counts for each wavelength of the reflected probe light beam. From above, the wavelength 501 nm is the isobestic wavelength.

Using these oxygen saturation ratios, the oximeter processor is able to determine the associated value for the percent $O_2$ Sat, i.e. the measure of oxygen saturation of the hemoglobin in the capillary bed.

Figure 3:
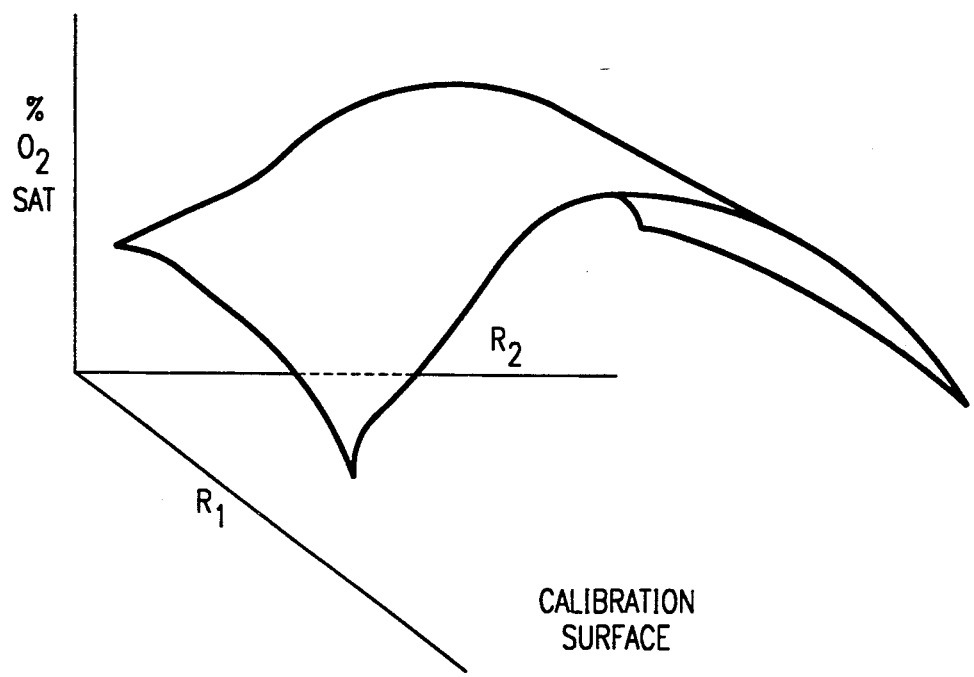
FIG. 3 is an exemplary plot of a calibration surface for percent oxygen saturation (% $O_2$ Sat) as a function of the oxygen saturation ratios $R_1$ and $R_2$ (this plot does not represent real data, but rather, is for illustrative purposes only).

FIG. 3 is an exemplary illustration of a plot of a calibration surface from which a value for percent $O_2$ Sat could be determined as a function of the oxygen saturation ratios $R_1$ and $R_2$. This plot does not represent real data, but is for illustrative purposes only.

Through appropriate programming in the oximeter processor, the laser oximeter can be used to systematically map oxygen saturation across the retina. For example, the oximeter processor could be programmed to scan the laser probe light across the eye in a predetermined pattern. At selected points, oxygen saturation ratios could be computed, and corresponding values of percent $O_2$ Sat determined and stored. From this data, a map of oxygen saturation could be developed and displayed (preferably using color coding).

3. Alternative Embodiments. The oximetry techniques of the invention can be generally applied to determining hemoglobin oxygenation in tissues that are optically accessible. In the case of non-ocular vascular beds, the oximetry techniques could be used to evaluate even subcutaneous tissues so long as they are optically accessible (such as by using an endoscope). Examples of such applications include peripheral vascular diseases (such as atherosclerosis or diabetes) and burns.

What is claimed is:

1. An oximetry method for determining hemoglobin oxygenation in optically-accessible tissue, comprising:
   probing a selected area of tissue with a source of collimated probe light of at least two predetermined wavelengths in an hemoglobin absorption band around an absorption isobestic wavelength of about 501 nm, with at least one wavelength being approximately the absorption isobestic wavelength, and at least one wavelength being non-isobestic;

detecting the probe light reflected from the tissue for each wavelength and providing corresponding reflection intensity signals; and in response to said reflection intensity signals, determining appropriate oxygen saturation ratios of reflection intensity for the absorption isobestic and the non-isobestic wavelengths representative of hemoglobin oxygenation.

2. The oximetry method of claim 1, wherein said probe light is provided by a multi-line source that provides said at least two wavelengths simultaneously.

3. The oximetry method of claim 2, further comprising the step of separating the reflected probe light into different wavelengths.

4. The oximetry method of claim 1, wherein said probe light is provided by a laser.

5. The oximetry method of claim 4, wherein said laser comprises a multi-line argon laser.

6. The oximetry method of claim 1, wherein the optically-accessible tissue is the inner retina of an eye, and wherein said probe light is directed to a selected capillary bed of the inner retina.

7. The oximetry method of claim 1, wherein said probe light comprises three wavelengths, one of which is isobestic, the other two being non-isobestic.

8. The oximetry method of claim 7, wherein said oxygen saturation ratios comprise a ratio R1 equal to the ratio of the reflection intensity signal for one non-isobestic wavelength to the reflection intensity signal for the absorption isobestic wavelength, and a ratio R2 equal to the ratio of the reflection intensity signal for the other non-isobestic wavelength to the reflection intensity signal for the absorption isobestic wavelength.

9. An oximeter for determining oxygen saturation in optically-accessible tissue, comprising:

a source of collimated probe light of at least tow predetermined wavelengths in an hemoglobin absorption band around an absorption isobestic wavelength of about 501 nm, the probe light being directed to a selected area of tissue and partially reflected from the tissue;

at least one wavelength being approximately the absorption isobestic wavelength, and at least one wavelength being non-isobestic;

an intensity detector for detecting the probe light reflected form the tissue for each wavelength and providing corresponding reflection intensity signals; and an oximeter processor responsive to said reflection intensity signals for determining appropriate oxygen saturation ratios of reflection intensity for the absorption isobestic and non-isobestic wavelengths representative of hemoglobin oxygenation.

10. The oximeter of claim 9, wherein said probe light source comprises a multi-line source that provides said at least two wavelengths simultaneously.

11. The oximeter of claim 10 further comprising separation optics for separating the reflected probe light into different wavelengths, said intensity detector including a separate intensity detection channel for each wavelength.

12. The oximeter of claim 9, wherein said probe light source comprises a laser.

13. The oximeter of claim 12, wherein said laser comprises a multi-line argon laser.

14. The oximetry method of claim 9, wherein the optically-accessible tissue is the inner retina of an eye, and wherein said probe light is directed to a selected capillary bed of the inner retina.

15. The oximeter of claim 9, wherein said at least two wavelengths of said probe light are located in the hemoglobin absorption band.

16. The oximeter of claim 9, wherein said probe light comprises three wavelengths, one of said wavelengths being the absorption isobestic wavelengths, and the other two wavelengths being non-isobestic.

17. The oximeter of claim 16, wherein said oxygen saturation ratios comprise a ratio R1 equal to the ratio of the reflection intensity signal for one non-isobestic wavelength to the reflection intensity signal for the absorption isobestic wavelength, and a ratio R2 equal to the ratio of the reflection intensity signal for the other non-isobestic wavelength to the reflection intensity signal for the absorption isobestic wavelength.

18. The oximeter of claim 17, wherein said intensity detector comprises a photon counter such that the oxygen saturation ratios are determined from photon counts for each wavelength.

19. The oximeter of claim 9, further comprising an ocular microscope for focusing said reflected probe light upstream from said intensity detector.

20. The oximeter of claim 9, further comprising oximeter optics, including said intensity detector, optically coupled to said ocular microscope for receiving said reflected probe light.

21. The oximeter of claim 20, wherein said oximeter processor comprises a computer coupled bidirectionally to said oximeter optics for controlling said oximeter optics, receiving said reflection intensity signals, and computing said oxygen saturation ratios.

22. The oximeter of claim 14, wherein said computer also controls said probe light source and implements an oximeter scanning program in which said probe light is scanned in a predetermined pattern around the eye to produce an oximeter map.

* * * * *